United States Patent [19]

Tomlinson

[11] 4,314,343

[45] Feb. 2, 1982

[54] METHOD AND APPARATUS FOR DETECTING AND INTEGRATING CHROMATOGRAPHIC PEAKS

[75] Inventor: Barrett L. Tomlinson, Santa Clara, Calif.

[73] Assignee: Spectra-Physics, Inc., San Jose, Calif.

[21] Appl. No.: 115,335

[22] Filed: Jan. 25, 1980

[51] Int. Cl.³ .............................................. G06F 15/20
[52] U.S. Cl. ................................. 364/498; 364/572; 364/733; 73/23.1
[58] Field of Search ............... 364/498, 497, 499, 500, 364/572, 724, 733; 73/23.1

[56] References Cited

U.S. PATENT DOCUMENTS

| | | | |
|---|---|---|---|
| 3,488,480 | 1/1970 | Stacy | 364/497 |
| 3,500,028 | 3/1970 | Killian | 364/497 |
| 3,555,260 | 1/1971 | Karohl | 364/497 |
| 3,562,501 | 2/1971 | Mears | 364/497 |
| 3,633,404 | 1/1972 | Chandler | 364/497 X |
| 3,757,261 | 9/1973 | Sather | 364/733 |
| 3,826,905 | 7/1974 | Valkama et al. | 364/498 X |
| 4,016,410 | 4/1977 | Eggermont | 364/733 X |
| 4,066,879 | 1/1978 | Leaver et al. | 364/498 |
| 4,180,857 | 12/1979 | Yoshihara et al. | 364/497 |
| 4,229,968 | 10/1980 | Muldoon | 73/23.1 X |

Primary Examiner—Edward J. Wise
Attorney, Agent, or Firm—Feix and Harrison

[57] ABSTRACT

Chromatographic peaks of varying width are detected and integrated by a method and apparatus that uses only the leading edge of the peak itself to detect the onset of the peak and to select for integration of the peak a filter detector having a time constant which matches the filter characteristics to the signal being monitored.

A plurality of filter detectors having different time constants are used for identifying the beginning of a peak. The output of all of the filter detectors is scanned to identify the onset of a peak, and the most appropriate filter detector is selected for integrating the peak.

6 Claims, 5 Drawing Figures

METHOD AND APPARATUS FOR DETECTING AND INTEGRATING CHROMATOGRAPHIC PEAKS

BACKGROUND OF THE INVENTION

This invention relates to method and apparatus for detecting and integrating chromatographic peaks.

In a typical chromatographic analysis the widths of the peaks normally vary by a factor of at least ten and usually by a factor of forty or so. Depending upon the particular analysis being run, there may be some pattern to the variation in the peak widths or there may be no pattern.

In using automated equipment for integrating the area under the peaks (to provide automated analysis of the samples being run), it is important to match the time constant of the filter detector used for integrating a peak with the width of the peak.

If the time constant of the filter detector is too short, the integrating equipment becomes insensitive to broad peaks. Broad peaks may be missed altogether, or all of the area under the peak may not be completely recovered.

If the time constant of the filter detector is too large, the automated equipment may miss peaks that are too narrow to be detected. The narrow peaks may look like noise. The automated equipment, in this case, might also tend to fuse adjacent narrow peaks together and integrate the fused peaks as one peak, rather than separately.

The prior art has varied the time constant of a filter detector as the chromatographic analysis is being run to try to match the filter detector to the signal being monitored.

In one prior art technique the assumption was made that the peaks will double in width ever so often. The time constant of the filter detector was adapted at specific times in a chromatogram to accommodate the predicted changes in the peak widths. This technique worked fairly well but had limitations, particularly with temperature or solvent programmed chromatograms.

A more recent technique measured the characteristics of a peak being integrated and then used that knowledge to predict the characteristics of a peak to be subsequently integrated. This technique also has undesirable limitations, particularly if there is too long a time interval between adjacent peaks.

SUMMARY OF THE INVENTION

It is a primary object of the present invention to avoid the problems presented by the prior art techniques of detecting and integrating peaks.

It is an important object of the present invention to use only the leading edge of the peak itself (1) to detect the onset of a peak and (2) to establish enough about the peak to be able to accurately determine the onset and the end of the peak.

It is a closely related object to use the leading edge of the peak to determine the characteristics of the peak which will follow at a time early enough to select for integrating the peak a filter detector which has a time constant appropriate for integrating that peak.

The method and apparatus of the present invention comprises a plurality of filter detectors for detecting a broad range of peak widths. The filter detectors are preferably tuned to slightly over-lapping ranges.

In a specific embodiment of the present invention analogue time-voltage data samples ae taken periodically as the chromatographic analysis is being run. The analogue time-voltage signals are converted to digital time-voltage integral signals, and a selected number of consecutive digital data sample signals are summed together to form a succession of data bunches with each data bunch having the same number of digital data sample signals.

The data bunches are fed in sequence to the input ends of a plurality of associated shift registers. Each location in each shift register corresponds to a discreet relative time position in the history of the data bunches.

In a specific embodiment the shift registers are connected serially. Each succeeding shift register has a bunch size which is twice as large as the bunch size in a preceding shift register.

A filter detector is connected to each shift register and computes the slope or curvature of the data bunches of the related shift register.

The output of all of the filter detectors is scanned to find the shift register and related filter detector having the smallest data bunch size which detects a slope larger than the threshold level.

The filter detector having the next larger time constant is then selected and used as the integrating filter to integrate the peak. This permits going back in time far enough to obtain time-voltage signals which can be used for baseline correction and also insures that the entire area under the peak is integrated.

Methods and apparatus for detecting and integrating chromatographic peaks having the features described above and effective to function as described above constitute specific objects of the present invention.

Other and further objects of the present invention will be apparent from the following description and claims and are illustrated in accompanying drawings which, by way of illustration, show preferred embodiments of the present invention and the principles thereof and what are now considered to be the best modes contemplated for applying these principles. Other embodiments of the invention embodying the same or equivalent principles may be used and structural changes may be made if desired by those skilled in the art without departing from the present invention and the purview of the appended claims.

BRIEF DESCRIPTION OF THE DRAWINGS

FIG. 4 also illustrates how each of the particular components that resides in a particular relative time position in a shift register is multiplied by a specific constant to compute a slope in the related digital filter.

FIG. 5 illustrates how the detector and integrator apparatus of the present invention uses the leading edge of the peak to detect the onset of the peak at a time early enough to make a decision on which filter detector is best suited for matching of a filter detector to the signal being monitored.

DETAILED DESCRIPTION OF PREFERRED EMBODIMENTS

Figure 1:
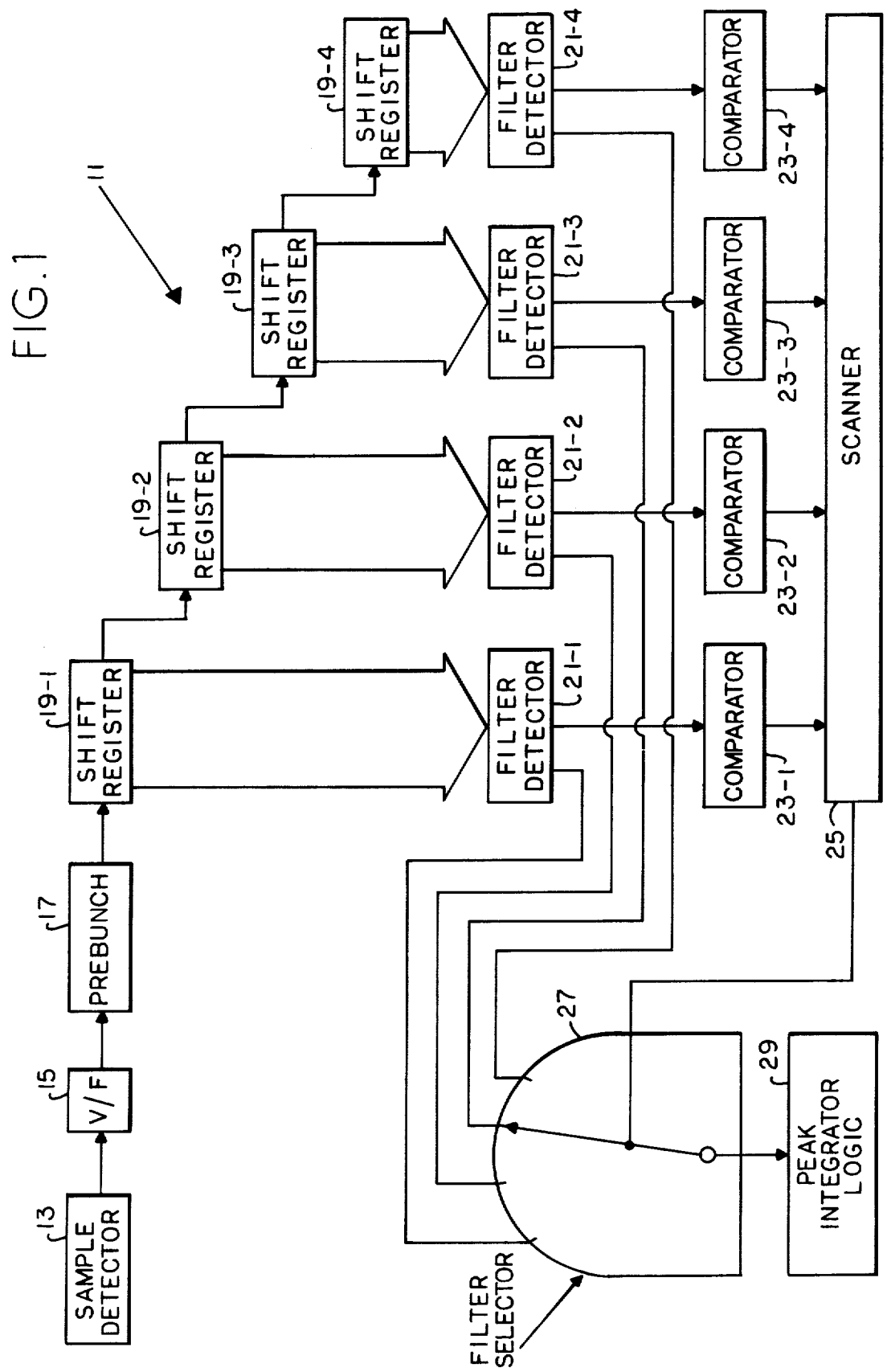
FIG. 1 is a schematic view of peak detecting and integrating apparatus constructed in accordance with one embodiment of the present invention.

A peak detecting and integrating apparatus constructed in accordance with one embodiment of the present invention is indicated generally in FIG. 1 by the reference numeral 11.

The peak detecting and integrating apparatus 11 includes a sample detector 13, a voltage to frequency converter 15, a prebunch summing apparatus 17 for bunching several consecutive data samples together to form a data bunch, a plurality of shift registers 19, a plurality of filter detectors 21 (each associated with one related shift register), comparators 23, a scanner 25, a filter selector 27 and peak integrator logic 29.

The sample detector 13 generates an analogue time-voltage data signal as the chromatographic analysis is being run. This signal is related to the instantaneous composition of the chromatographic column effluent and is fed into an oscillator 15 whose output frequency depends on the input voltage. The oscillator 15 emits pulses which are counted for an integral number of power line cycles. The pulse count is fed to the prebunch 17. The prebunch 17 groups (sums) one or more data samples together and feeds them to the shift register 19.

The output of the v/f converter and counter 15 is thus not a measure of instantaneous voltage but is a time voltage integral, and consecutive readings can be summed by the prebunch summer 17 to estimate the input voltage with greater accuracy with increased summing of consecutive voltage readings. Lumping several bunches together therefore increases the precision of the voltage reading and allows the apparatus 11 to detect the presence of smaller peaks. The summing of the data samples together also increases the noise filtering. By increasing the time duration of the data bunch, the sensitivity of the voltage integral to high frequency noises is decreased.

For purposes of quantitating very small peaks the optimal size data bunch is just small enough to permit detection of the chromatographic peaks of interest.

The shift registers 19 maintain a serial history of the data bunches read from the analogue to digital converter 15.

Figure 3:
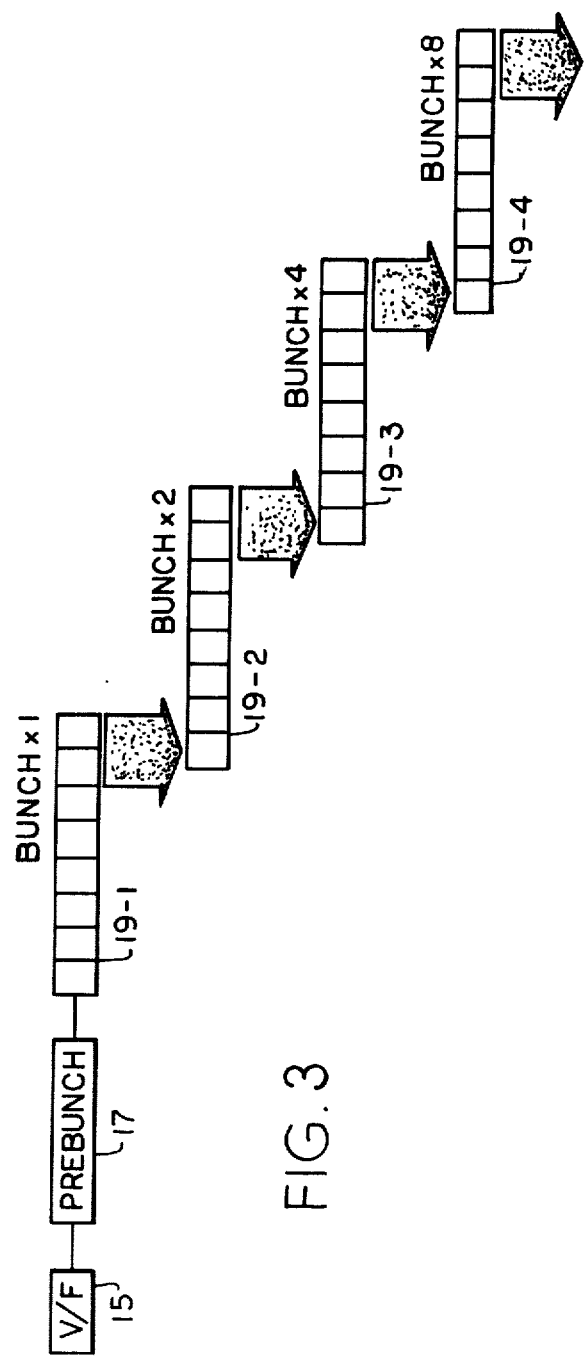
FIG. 3 is a fragmentary view showing how the shift registers of FIG. 1 are, in one specific embodiment of the invention, connected serially. The data bunches which are shifted out of one register are grouped in pairs at the inlet to a succeeding shift register.

In the particular embodiment illustrated in the drawings, the shift registers 19-1, 19-2, etc., are shown connected in series, and the data bunches at the outlet of each shift register are paired (as shown in FIG. 3) for the input to the next succeeding shift register. The data bunches are therefore increased by powers of two as they shift from one shift register to the next shift register.

In a specific embodiment of the present invention eight shift registers are used so that the bunch size in the last shift register is 128 times the bunch size in the first shift register.

Also, in a specific embodiment of the present invention, each shift register has twelve logical locations (indicated by the letters A through L in FIG. 4) with each location corresponding to a discreet relative time positon in the serial history of the data bunches of the chromatogram.

Each time a new data bunch is completed it is shifted into the shift regiser 19-1, and the related filter detector 21-1 computes a slope for all the data bunches in the shift register 19-1 according to the following formula (where A equals the most recent data bunch, B equals the next most recent data bunch, etc.):

$$Slope = 11 \times A + 9 \times B + 7 \times C + 5 \times D + 3 \times E + F - G - 3 \times H - 5 \times I - 7 \times J - 9 \times K - 11 \times L.$$

Figure 4:
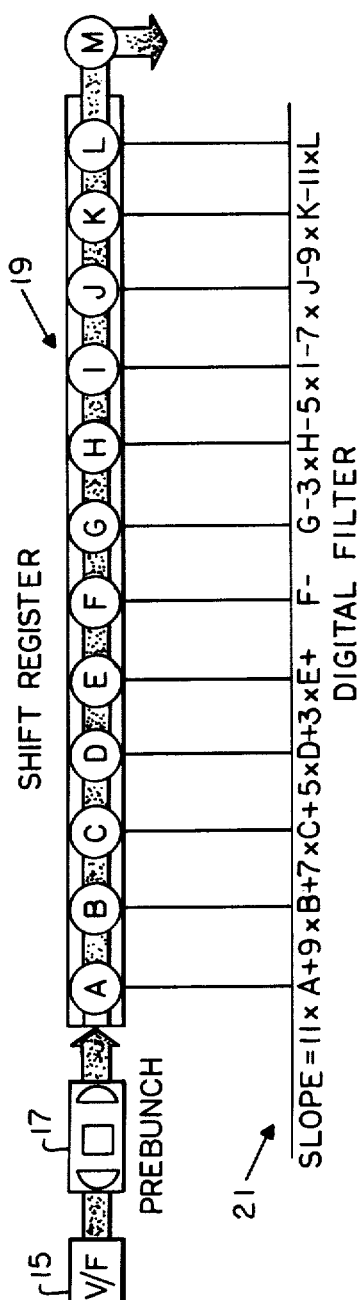
FIG. 4 is a fragmentary view illustrating how each position in a shift register corresponds to a discreet relative time position to provide a serial history of the data bunches shifted through the shift register.

This operative relationship of the filter detector with a related shift register 19 is also illustrated in FIG. 4.

In a specific embodiment a slope of one microvolt/second corresponds to a slope reading of 57.2 using standard parameters of PW=6, where PW equals the number of power line cycle integrals grouped in a data bunch by the prebunch 17. At PW=1 the sensitivity is 1.58 counts of slope for a true slope of 1 microvolt/second. For a constant slope signal (in units of volts/second) the computed slope values according to the above equation will change according to the square of the ratio of the two bunch sizes used in the calculations, i.e.

$$Slope\ (for\ PW=A) = (A/B)^2 \qquad Slope\ (for\ PW=B).$$

The output of each digital filter 21 is fed to a comparator 23 which compares the filter output with a preset threshold and which produces a yes or no signal (peak or not a peak). The scanner 25 scans each comparator 23 to see whether a peak has been detected by any of the filter detectors 21.

When a peak is detected, the scanner 25 acts, in association with a filter selector 27 (shown as a rotary switch for purposes of illustrating functional operation), to select the most appropriate one of the filter detectors 21 as the filter detector to be used for integrating the peak by the peak integrator logic 29, as will be described in more detail below.

While the shift registers 19 have been described and are illustrated as connected in series, the shift registers can be in parallel. The data bunches fed into the various shift registers are grouped in different bunch sizes in both cases.

Figure 2:
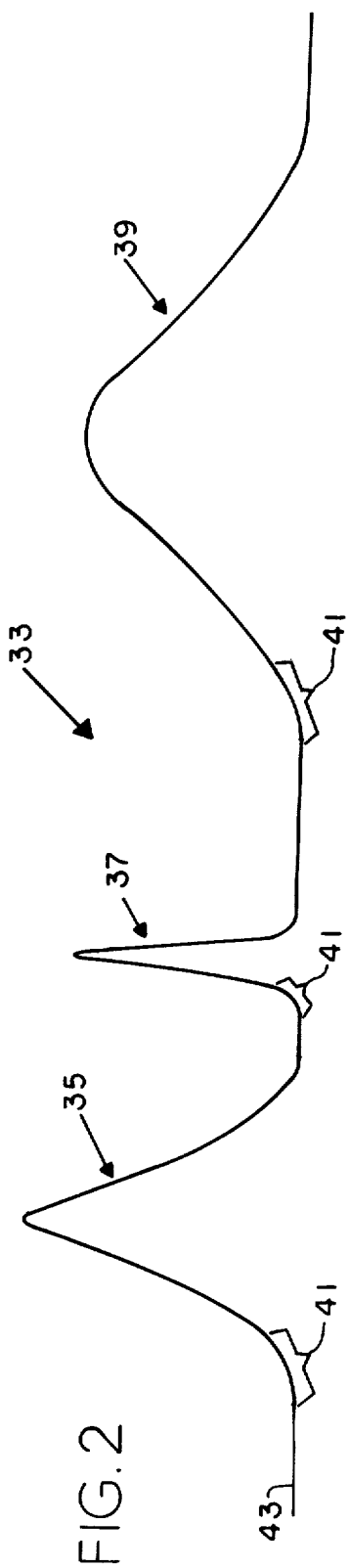
FIG. 2 is a chromatogram showing peaks of varying width which are detected and integrated by the apparatus and method of the present invention.

A chromatograph having peaks to be integrated is indicated generally by the reference numeral 33 in FIG. 2. The chromatogram 33 shown in FIG. 2 has three peaks 35, 37 and 39 of varying widths, and the present invention operates, with no prior knowledge of the chromatogram 33, to detect each of the peaks 35, 37 and 39 using only the information developed from the onset of the peaks (within the regions generally indicated by the reference numerals 41) as the peaks begin to depart from the baseline 43.

The present invention also uses the information determined from the detection of the onset of the peak to select one of the filter detectors 21 as the most appropriate filter for integrating the peak in the peak integration logic 29.

The baseline 43 is established whenever the slopes computed using the serial bunch history are smaller in magnitude than a peak threshold value for a prolonged number of bunches.

Once the baseline is established, a peak is detected whenever the computed slope value is more positive than the peak threshold for two consecutive bunches. The slope must remain positive for ten bunches to confirm the peak in a specific embodiment of the present invention, and from the point of detection this embodiment of the present invention backs up eight bunches and then uses the sum of the prior sixteen bunches as the baseline level. The peak integration begins at the midpoint of the baseline reference (i.e., sixteen bunches before the bunch that triggered the peak).

The bunch size used for integration is selected to be twice as large as the bunch size used for detection.

Figure 5:
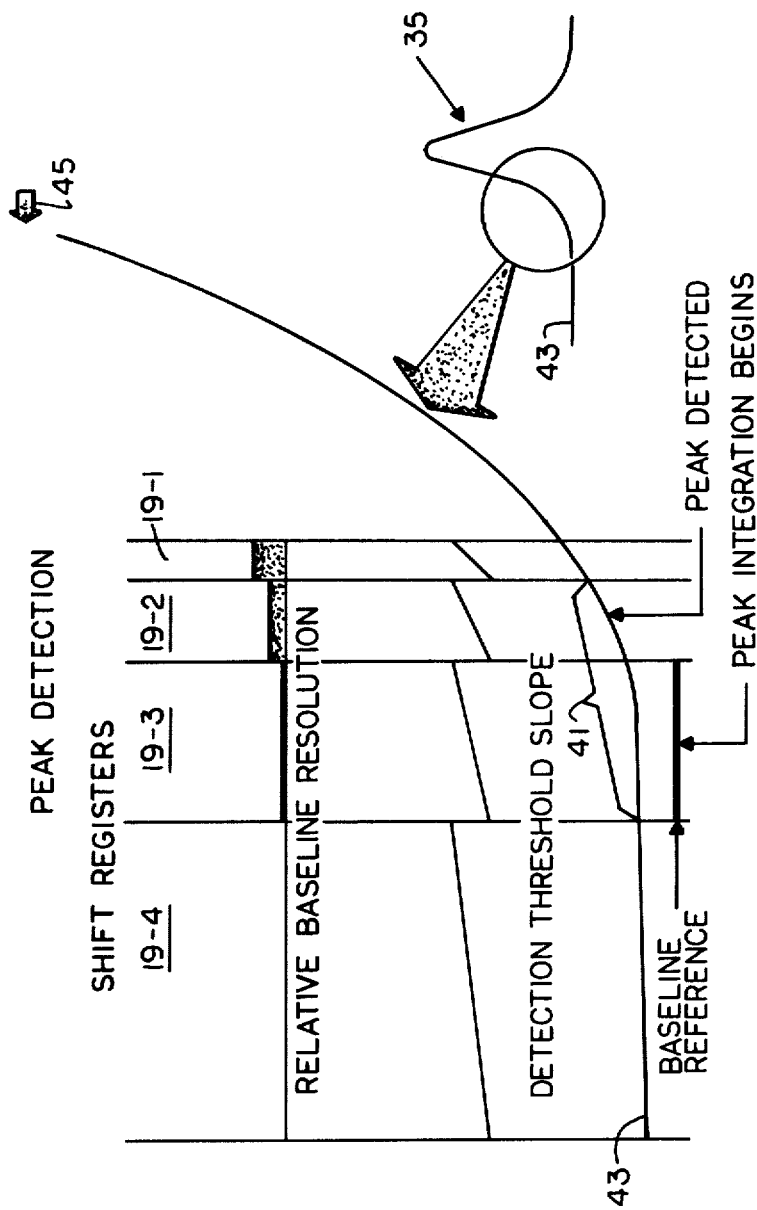
FIG. 5 is a diagrammatic view which illustrates the dynamic interrelationship between the signal being monitored and the operation of the filter detectors of the present invention.

This mode of operation is graphically illustrated in FIG. 5.

Looking at FIG. 5, the peak 35 is moving leftward into the shift registers in the direction indicated by the block arrow 45. That is, the data samples being taken during the chromatographic analysis are bunched and fed into the shift registers 19-1, 19-2, 19-3, etc., in the order graphically illustrated in FIG. 5.

As illustrated in FIG. 5 the width of the peak 35 is such that the first filter detector 21-1 does not detect the onset of the peak (at the portion of the peak then being sampled by that filter detector) because the time constant for that filter detector is too small for that part of the curve of the peak.

The next filter detector 19-2 does detect the onset of the peak 35 because the curve slope of the peak exceeds the threshold level for two data bunches in the filter detector 19-2.

The filter detector 19-3 is then selected by the scanner 25 and the filter selector 27 as the filter detector which is used to integrate the peak. Selecting this filter detector at the onset of the peak permits going back in time far enough to obtain a voltage reference that is used for the baseline correction which providing the desired matching of the filter characteristics to the signal being monitored.

The shifting of the data samples through the bunch history is such that the attempt to detect a peak is first made on a small bunch size and then made with progressively larger bunch sizes. If a large bunch size does effectually detect a peak, the smallest bunch size is probably far into the peak, perhaps even over the crest of the peak by the time the peak is actually found. This can be seen by reference to FIG. 5 which shows that the bunch size for the shift register 19-1 is well into the peak by the time that the peak is detected by the filter detector 21-1 corresponding to the next larger bunch size.

The peak crest is located by identifying the time and level of the largest bunch between the beginning baseline level and the time that the computed slope becomes negative and greater in magnitude than the peak threshold.

To evaluate the peak width, the number of bunches from the maximum bunches at the peak crest and the level halfway between the beginning baseline and level and the peak maximum are counted. The resulting number of bunches is multiplied by the number of data samples per bunch and recorded as peak width, if requested.

The integration of the peak proceeds in a conventional manner as is well known in the art.

This integration is also described in the SP 4100 Computing Integrator Instruction Manual, part number A0099-085 printed as 0017 in March 1979 and revised in September 1979. This manual is distributed by the assignee of the application and is incorporated by reference in this application.

The integration of a peak is normally terminated either by finding baseline on a tangent fit or by detecting an integration inhibit condition.

To find baseline a slope must be less than the peak threshold value for five integration size bunches and must have had more bunches with slope of more magnitude than the peak threshold than there were bunches in the peak width measurement.

A tangent fit is found from the beginning baseline if the present level is lower than the beginning baseline level and the local slope at the tangent fit point is negative and smaller in magnitude than the slope computed from the beginning baseline reference to the current data bunch.

The ending baseline reference level is the sum of eight consecutive integration size data bunches symmetrically distributed about the point at which the peak is terminated.

In the particular embodiment of the invention illustrated in the drawings the filter detectors are digital filters. However, other filter detectors, such as operational amplifiers, can be used. Other equations for determining slope or curvature in the filter detectors can also be used, and the number of elements in the shift registers can vary. The filter detectors 21 can be embodied in read only memory, and the detectors can compute curvature rather than slope.

The peak detecting and integrating apparatus 11 as described above has the ability to optimize the parameters used in peak integration. The optimization is done by choosing the bunch size and peak thresholds which are most appropriate for the peak being integrated. Bunch size optimization is accomplished by allowing a number of bunch sizes (eight bunch sizes in one embodiment of this invention) to compete for the right to integrate a specific peak. The bunch sizes are PW, $2 \times$ PW, $4 \times$ PW, ... $128 \times$ PW.

Bunches which are shifted out of the PW sized bunch shift register 19-1 are grouped in pairs of two and shifted through the succeeding shift registers, each bunch having size $2 \times$ PW. Bunches shifted out of the $2 \times$ PW history set up are paired and fed into the $4 \times$ PW bunch history, and so on. Each time a bunch is shifted, a slope is calculated using the entire bunch history and pairs of bunches from the next lower size bunch history. The first PW history whose slope exceeds its corresponding peak threshold for two consecutive bunches triggers the integration state. The next larger PW than the PW which triggers integration is selected for purposes of integrating until baseline is again seen. The effective peak threshold is chosen to be proportional to bunch size, with the peak threshold parameter defining the value used for the smallest bunch size.

While I have illustrated and described the preferred embodiments of my invention, it is to be understood that these are capable of variation and modification, and I therefore do not wish to be limited to the precise details set forth, but desire to avail myself of such changes and alternations as fall within the purview of the following claims.

I claim:

1. In a method of integrating peaks in a chromatographic analysis of the kind in which time varying signals are fed to a filter detector which detects weighted average slope or curvature over a time period in order to detect the presence of the peak to be integrated, the improvement comprising, using a multiplicity of filter detectors having different averaging time periods for detecting the presence of a peak, scanning the output of the filter detectors to find a detecting filter detector whose output detects the presence of a peak, then selecting as the integrating filter detector a filter detector whose averaging period is closely matched to the shape of the detected peak as detected by the detecting filter detector, and integrating the peak with the selected filter detector.

2. A method of detecting and integrating peaks in a chromatographic analysis and comprising, converting an analogue time-voltage signal to a digital representation, feeding the digitized signal to a plurality of digital filters, the output signals of which represent a weighted average curvature or slope over various length time periods, scanning the outputs of the digital filters to select one whose averaging period is comparable to the width of the peak to be integrated, and integrating the peak using the selected digital filter.

3. The invention defined in claim 2
wherein the digital filters have averaging periods differing by factors of two, and
wherein the digital filter selected to integrate the peak has an averaging time period twice as long as the filter with the shortest period whose output first exceeds a threshold value during the onset of the peak.

4. In apparatus for integrating peaks in a chromatographic analysis of the kind in which time varying signals are fed to a filter detector which detects weighted average slope or curvature in order to detect the presence of the peak to be integrated, the improvement comprising, filter detector means comprising a multiplicity of filter detectors having different averaging time periods for detecting the presence of a peak, scanning means for scanning the output of the filter detectors to find a detecting filter detector whose output detects the presence of a peak, selecting means for selecting as the integrating filter detector a filter detector whose averaging period is closely matched to the shape of the detected peak as detected by said detecting filter detector, and integrating means for integrating the peak with the integrating filter detector.

5. Apparatus for detecting and integrating peaks in a chromatographic analysis and comprising, converter means for converting an analogue time-voltage signal to a digital representation, feeding means for feeding the digitized signal to a plurality of digital filters, the outut signals of which represent a weighted average curvature or slope over various length time periods, scanning means for scanning the outputs of the digital filters to find a detecting digital filter with the shortest length time period which detects the presence of a peak, selecting means for selecting as the integrating filter a filter whose averaging period is comparable to the width of the peak to be integrated as detected by said detecting digital filter, and integrating means for integrating the peak with the integrating filter.

6. The invention defined in claim 5
wherein the digital filters have averaging periods differing by factors of two, and
wherein the integrating digital filter selected to integrate the peak has an averaging time period twice as long as the detecting digital filter with the shortest period whose output first exceeds a threshold value during the onset of the peak.

* * * * *